US009387043B2

(12) United States Patent
Yang et al.

(10) Patent No.: US 9,387,043 B2
(45) Date of Patent: Jul. 12, 2016

(54) MEDICAL MASTER/SLAVE TYPE DEVICE FOR MINIMALLY INVASIVE SURGERY

(75) Inventors: Guang-Zhong Yang, Surrey (GB); George Mylonas, London (GB); Christopher Payne, London (GB)

(73) Assignee: Imperial Innovations Limited, London (GB)

( * ) Notice: Subject to any disclaimer, the term of this patent is extended or adjusted under 35 U.S.C. 154(b) by 234 days.

(21) Appl. No.: 14/116,752

(22) PCT Filed: May 14, 2012

(86) PCT No.: PCT/GB2012/051070
§ 371 (c)(1),
(2), (4) Date: Feb. 3, 2014

(87) PCT Pub. No.: WO2012/153152
PCT Pub. Date: Nov. 15, 2012

(65) Prior Publication Data
US 2014/0171964 A1   Jun. 19, 2014

(30) Foreign Application Priority Data

May 12, 2011   (GB) .................................. 1107937.3
May 18, 2011   (GB) .................................. 1108320.1

(51) Int. Cl.
*B25J 19/02*   (2006.01)
*A61B 19/00*   (2006.01)
(52) U.S. Cl.
CPC ..... *A61B 19/2203* (2013.01); *A61B 2034/2048* (2016.02)

(58) Field of Classification Search
CPC .................... A61B 19/2203; A61B 2019/2223
USPC ..................................................... 318/568.16
See application file for complete search history.

(56) References Cited

U.S. PATENT DOCUMENTS

| 5,784,542 | A | 7/1998 | Ohm et al. |
| 5,876,325 | A | 3/1999 | Mizuno et al. |
| 2004/0243147 | A1 | 12/2004 | Lipow |

FOREIGN PATENT DOCUMENTS

| WO | WO 2006/057702 A2 | 6/2006 |
| WO | WO 2007/033379 A2 | 3/2007 |
| WO | WO 2009/023801 A1 | 2/2009 |
| WO | WO 2009/100368 A1 | 8/2009 |

OTHER PUBLICATIONS

A. Degani et al., "Highly Articulated Robotic Probe for Minimally Invasive Surgery." Proceedings of the 2006 IEEE International Conference on Robotics and Automation, Orlando, Florida—May 2006, pp. 4167-4172, May 15, 2006.
T. Ota et al., "A Highly Articulated Robotic Surgical System for Minimally Invasive Surgery." The Annals of Thoracic Surgery, vol. 87, No. 4, pp. 1253-1256, Apr. 1, 2009.

*Primary Examiner* — Erick Glass
(74) *Attorney, Agent, or Firm* — Blank Rome LLP

(57) ABSTRACT

Apparatus for Minimal Invasive Surgery (MIS) comprising a master device, a slave device, a detector for detecting a parameter of, or associated with the slave device, and a shape locking system for locking the shape of the master device in response to a parameter detected by the detector.

19 Claims, 9 Drawing Sheets

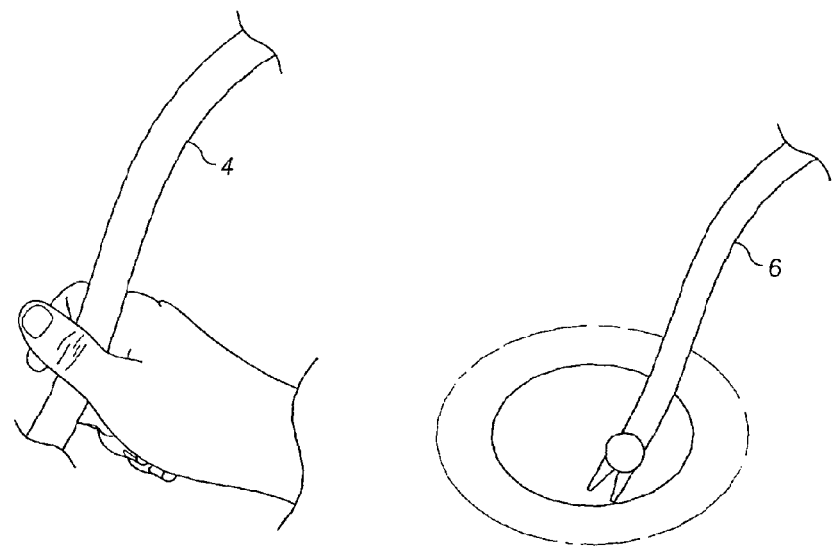
FIG. 5
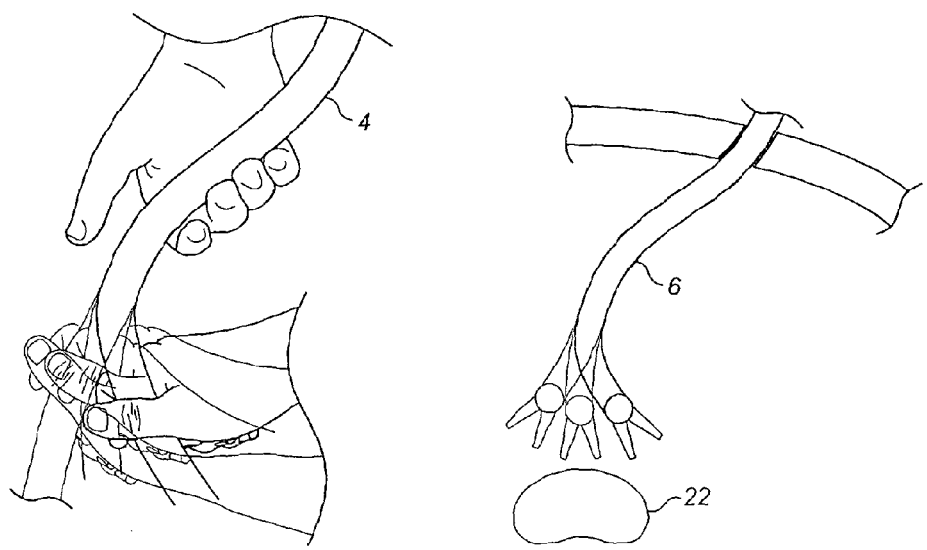
FIG. 6a                    FIG. 6b

MEDICAL MASTER/SLAVE TYPE DEVICE FOR MINIMALLY INVASIVE SURGERY

This invention relates to a device suitable for use in Minimal Invasive Surgery (MIS), and to a user interface for such a device.

MIS has become more widespread in recent years due to recent technological advances in surgery which enable earlier intervention, consistent surgical outcome, and accelerated patient recovery.

MIS can be robotically assisted to achieve improved quality, accuracy and consistency.

In robotic surgery, dexterity is generally enhanced by microprocessor controlled mechanical wrists, which allow motion scaling for reducing gross hand movements and improved performance of micro-scale tasks. A known system, for example, consists of a surgeon's console, a patient-side cart, a high-performance 3D vision system, and proprietary endo-wrist instruments. This system allows the surgeon to operate while seated at the console viewing a magnified stereo image of the surgical field. The surgeon's hand-wrist manoeuvres are then seamlessly translated into precise, real-time movements of the surgical instruments inside the patient.

The continuing evolution of the technology, including force feedback and virtual immobilization through real-time motion adaptation, will permit more complex procedures such as beating heart surgery to be carried out under a static frame-of-reference. Current systems for human robot interaction are generally based on mechanical systems either using standard input devices or bespoke designed master-slave manipulators.

For example, mechanical input 'joystick-like' devices are commonly used as a control input for many applications including robotic surgery. However other control methods have also been adopted such as eye tracking, voice control in the medical robotics field as well as other methods like vision techniques, inertial sensors, and IR sensors in the wider field of human-machine interfaces.

Since most of the current robotic systems use rigid instruments, the control interface only needs to employ a roll-pitch-yaw mechanism to control the end effector. Other control interfaces can also be added to control the instrument, e.g., opening/closing of a surgical grasper.

With the current pursuit of minimally invasive surgery is the development of articulated instrumentation to provide flexible access to a surgical site from the point of incision. In these applications, simple control interfaces are no longer suitable to map the higher degrees of freedom required for flexible robots. In many cases, the surgical instrumentation does not have line-of-sight and must follow a curved path so as to be able to reach a destination within the surgical environment, as is the case during endoscopy or single incision laparoscopy.

In other cases, articulation is required to provide triangulation of surgical instruments to either provide a mechanical advantage for tissue manipulation or to allow the surgeon to manipulate the tissue from a plurality of orientations, making the surgery easier and quicker for the surgeon to perform where access is limited.

Whilst flexible access provides dexterity within the patient, the method by which the surgeon commands the slave manipulator becomes increasingly unintuitive as the degree of articulation in the slave increases. This occurs when there is a disparity in the configuration of the human arm/hand/wrist and the slave and/or when the slave has more degrees of freedom than can be controlled by the human arm/hand/wrist.

In the case of a hyper-redundant, snake-like device the master input cannot be directly mapped to the human arm/hand/wrist.

It is known that haptic (force feedback) can help replace some of the sensory feedback that is lost in minimally invasive surgery due to the restricted access between the surgeon and the surgical site. This sense of touch is completely lost in a master-slave robotic system unless the contact forces between tool and tissue can be measured or inferred and fed-back to the user.

A number of commercial haptic devices (position input, force output) are available and are used in robotic master-slave surgical systems for both research and commercial systems. Such manipulators however are generally of the 6 DoF (Degrees of Freedom) stylus or parallel mechanism type which can be used to intelligently control a kinematically complex slave device (for example with path following of the end-effector).

According to a first aspect of the present invention there is provided an apparatus for MIS comprising a master device, a slave device, a detector for detecting a parameter of, or associated with the slave device, and a shape locking system for locking the shape of the master device in response to a parameter detected by the detector.

The slave device may therefore comprise a robotic device which may be controlled by the master device to enable a skilled person such as a surgeon to carry out a procedure using minimal invasive surgery.

The inventors have realised that by incorporating a shape locking mechanism that it is adapted to lock the shape of the master device in response to one or more parameters of, or associated with the slave device, a haptic interface between the user and the slave device is created.

Further, because the haptic interface is created through locking the shape of the master device to thereby prevent further movement of the master device and the slave device, the haptic interface is a passive haptic interface since the only forces exerted on the user are those generated from reaction forces generated by the user for example pushing against the locked master device.

Because the movement of the slave device is caused by movement of the master device, if the master device is locked in a particular position, then the slave device will be held in a corresponding position without having to utilise means for directly locking the shape of the slave device.

Although master/slave robotic surgery tools incorporating haptic interfaces are known, known haptic interfaces are active rather passive. Further, any known haptic interface comprising a shape locking system is one in which it is the slave device rather than the master device, the shape of which is locked. In such systems, it is necessary to have further devices such as sensor and motors to measure the position of the haptic device (the slave device in known systems) and then exert forces on the user in response thereto.

An advantage of the invention is therefore that no such additional devices are required in order to provide haptic feedback, and further the haptic feedback is passive.

The use of a passive rather than an active haptic system is advantageous when the slave device is used in a surgical application. This is because active haptic systems can become unstable particularly in the simulation of hard impacts and sudden disturbances. Such instability is unacceptable during a surgical application and could cause harm to a patient's body.

The master device and the slave device may be operatively connected to one another such that movement of the master device maps directly onto the slave device. In other words, an operator, such as a surgeon may control movement of the slave device via movement of the master device in such a way that a movement of the master device results in the corresponding movement of the slave device.

This may be achieved by shaping the slave device so that it has a similar shape to that of the master device.

In some embodiments of the invention, the master device and the slave device each have the same architecture.

In other words, the master device and the slave device may have the same shape and configuration as one another, and because the movement of the master device may map directly onto the slave device, operation of the apparatus becomes more intuitive. In addition, because the master device has the same shape as the slave device, the master device may have the same number of degrees of freedom as the slave device.

The master device and the slave device may have any desirable configuration, and in some embodiments, the master device and the slave device each comprise a hyper-redundant (or snake like) robotic instrument.

As mentioned hereinabove, it has hitherto not been possible to have direct mapping between a master device and a slave device in a system suitable for minimal invasive surgery, when the slave device comprises a hyper-redundant, snake like device. This is due to the high number of the degrees of freedom that exists in such a snake like device.

Both the master device and the slave device may be viewed as tube devices. Further, the master device may be viewed as a shape lockable tube device.

An apparatus according to embodiments of the present invention may be used in conjunction with the "active constraint" or "virtual fixture" concept. An active constraint, in the context of a surgical robot, is a predefined space in which a robot is free move. As the robot is moved towards a boundary, the robot applies a force normal to the boundary forcing the user to keep the robot within the boundary. This may be useful, for example, when the surgeon wants to manipulate a sharp tool within a surgical environment and wants to ensure the tool does not contact the patient's body in an undesirable location such as near a blood vessel.

In the context of the present invention, this means that if the slave device is caused to move by a user into a location that is outside the boundary, the shape locking system may be activated in order to lock the shape of the master device. This will provide haptic feedback preventing further movement of the slave device.

The invention may further comprise a detector for detecting the position of the slave device relative to a boundary, such as a geometric boundary.

The boundary may be determined pre-operatively, or may be acquired in-vivo using, for example techniques or by measurements using for example ultrasonic sensors, a laser system etc.

In such embodiments of the invention the detector may be attached to or positioned close to the slave device and may be adapted to detect the presence of an object, and to signal to the shape locking system when any object is within a certain predetermined distance from the slave device.

The position of the slave device may be determined in other ways. For example, when the apparatus incorporates a computer screen contained in the console, for example, sensors may be used to determined the position of the slave device and then to use this information to enable the position of the slave device to be graphically represented on the computer screen. Software may then be used to determine when the graphical representation of the slave device touches, or approaches a boundary also represented on the computer screen.

Such a detector could be used in embodiments of the invention in which shape locking mechanism causes the master device to become progressively stiffer as the slave device approaches a boundary and to thereby indicate to an operator that the slave device is close to the boundary.

In other embodiments, the detector may comprise one or more sensors associated with the slave device, which sensors are adapted to measure contact forces. In such embodiments, when there is contact between the slave device and something in its environment, the shape locking system may be activated in order to lock the master device thus preventing further movement of the slave device.

Alternatively, or in addition, the one or more sensors may be adapted to measure torques.

The shape locking system may be used to simplify the control of the slave device in embodiments of the invention where the slave device comprises a hyper-redundant in snake like robot.

In such embodiments, the master device may be used to manipulate the slave device into a gross position and then may be partially locked by the shape locking system at some predetermined point along the length of the master device. This results in distance manipulation of the slave device being possible after a portion of the proximal end of the master device had been locked. This enables the operator to manipulate the slave device with fewer degrees of freedom being available thus simplifying the controls of the device.

Such an approach makes use of the hyper-redundant nature of the slave device which allows flexible access and in-vivo navigation, but at the same time offers simplified and intuitive control during complex surgical tasks.

Furthermore, once a portion of the master device has been locked, it is clear to a user what configuration/path has been taken by the slave device. This should allow for enhanced orientation during surgery.

In other words, embodiments of the invention may comprise a shape locking system which is adapted to lock a part only of the master device. In particular, the shape locking system may be adapted to lock a proximal portion only of the master device to thereby allow distal manipulation only of both the master device and the slave device.

In embodiments of the invention, the apparatus may comprise a trigger to enable an operator to switch on the shape locking system either partially or totally.

The switch may take any convenient form and may for example be in the form of a mechanical switch, or may be a trigger controlled by computer algorithm or other control means.

The apparatus may further comprise an actuator for actuating the shape locking system.

The actuator may be in the form of, for example, a motor, such as a DC motor although other types of actuator could also be used as appropriate, for example a linear servomotor, pneumatic/hydraulic actuations, solenoid actuation, shape memory alloy, piezoelectric motor, electromagnetic motor etc.

The actuator may be operatively connected to the detector to activate the shape locking system in response to signals transmitted by the detector relating to the position of the slave device.

The master device may comprise a plurality of shape lockable elements positioned axially along the length of the master device, which elements are shaped to engage with one another.

The device may further comprise a tendon extending along the length of the master device. In such embodiments of the invention, the actuator is adapted to introduce tension into the tendon in order to lock the segments together.

The device may comprise a plurality of tendons extending along the length of the master device.

Adjacent segments may be shaped such that a friction shape lock is achieved through the tensioning of the tendon or tendons.

In other embodiments of the invention, each element may comprise a lock portion adapted to engage with a corresponding lock portion on an adjacent element.

In such an embodiment, adjacent elements will lock together only in a particular relative orientation once plurality of relative orientations in which the respective lock portions are positioned to engage with one another.

Each element may comprise a plurality of lock portions each of which lock portions is adapted to engage with the corresponding one of a plurality of lock portions on an adjacent element.

In a particular embodiment, each element comprises a plurality of pits at one end and bumps at an opposite end, the pits being shaped and located to engage with corresponding bumps on an adjacent element, and vice versa.

In such an embodiment, when the elements are pulled together due to tension created by the tendon or tendons, a pit formed on a first element will locate and engage with a corresponding bump on an adjacent element, and vice versa.

Such arrangement will provide a mechanical constraint between adjacent segments when tension is applied to the tendon rather than relying merely on friction between adjacent elements.

The apparatus may further comprise a sensor for sensing the shape of the master device.

The apparatus may comprise a plurality of such sensors.

The sensors may comprise inertial sensors such as accelerometers and gyroscopes, as well as magnetometers used to obtain the rotation in the plane normal to gravity.

The sensor may be used to determine the position and the orientation of all parts of the master device relative to the initial starting position and orientation of the master device.

By determining the position and orientation of all parts of the master device, positional information may be transmitted to the slave device in order that the slave device is able to take a corresponding position and orientation.

The apparatus may further comprise a master console operatively positioned between the master device and the slave device. The master console may comprise a surgical console which provides a platform from which the surgeon may operate the slave device in order to enable natural orifice or single incision surgery to be carried out.

The apparatus may comprise more than one master device and a corresponding number of slave devices.

In a particular embodiment, the apparatus comprises two master devices and two slave devices.

In such an embodiment, a user is able to hold one master in each hand. Such a system is known as a bi-manual system.

According to a second embodiment of the present invention there is provided a method of carrying out minimal invasive surgery using an apparatus according to a first aspect of the present invention.

The invention will now be further described by way of example only with reference to the accompany drawings in which.

Figure 2:
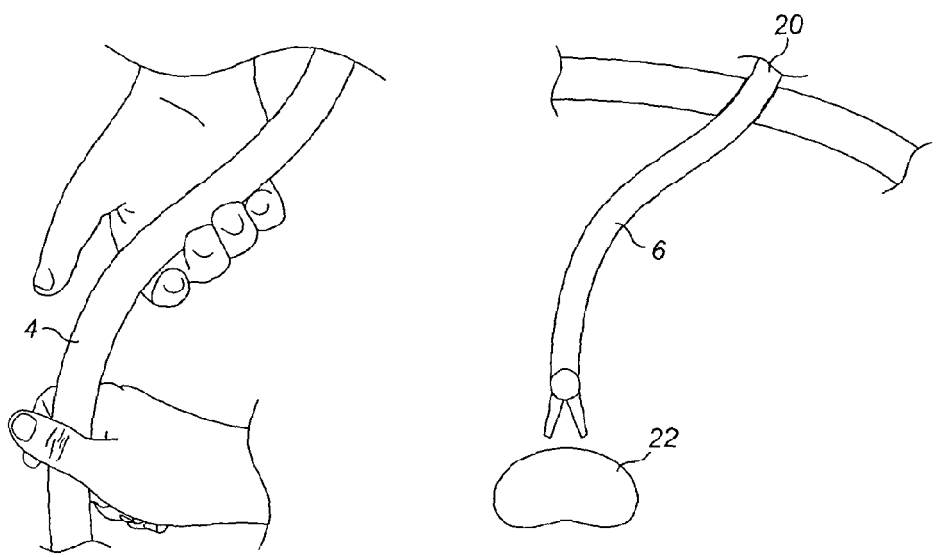
FIG. 2 is schematic representation showing a master device in the form of a tube being manipulated, and a slave device conforming to the shape that the master device takes.
Figure 3C:
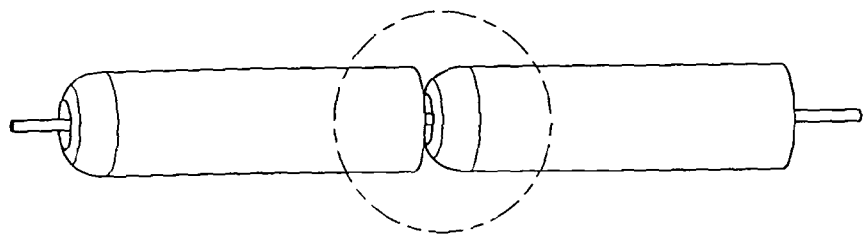
Figure 3B:
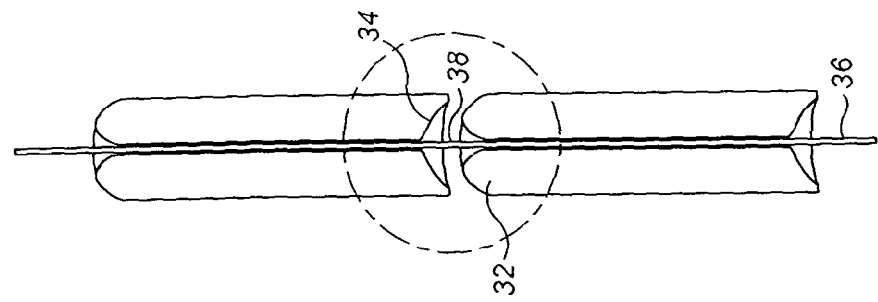
Figure 3A:
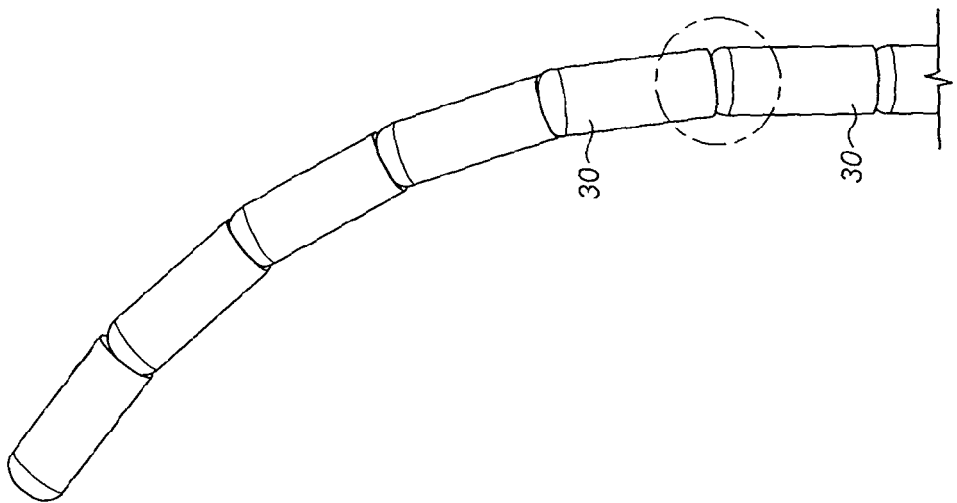
Figure 4A:
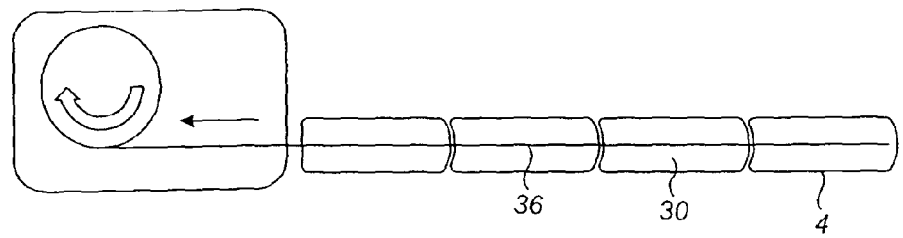
Figure 4B:
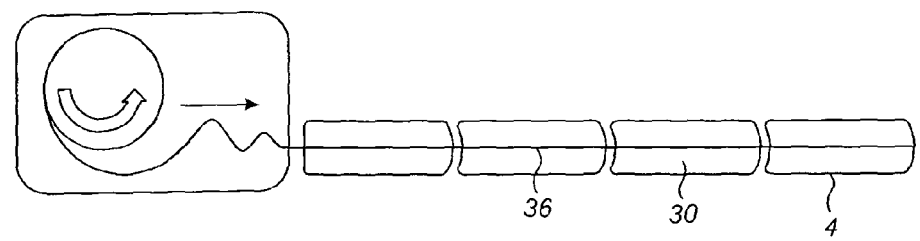
Figure 4C:
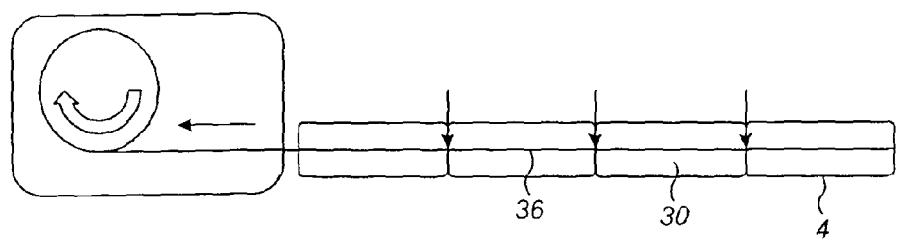
Figure 7:
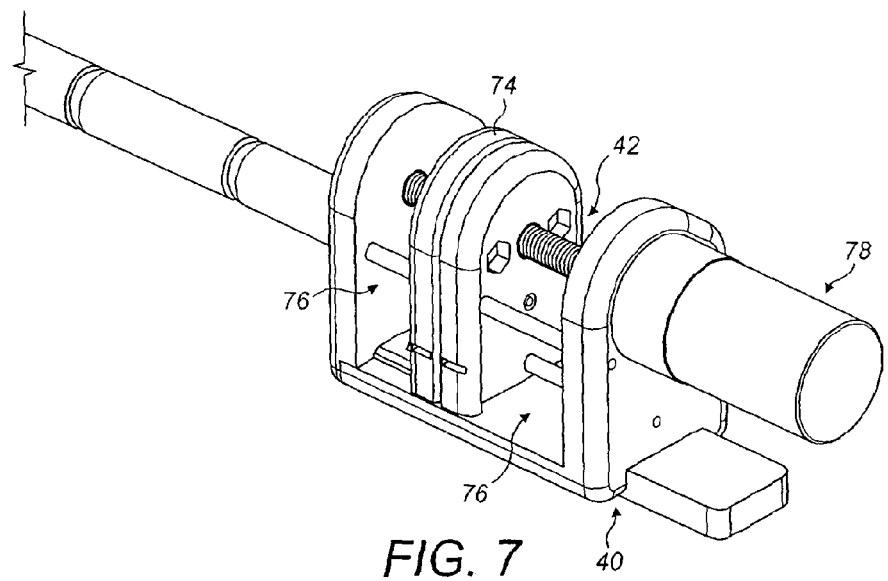
Figure 8:
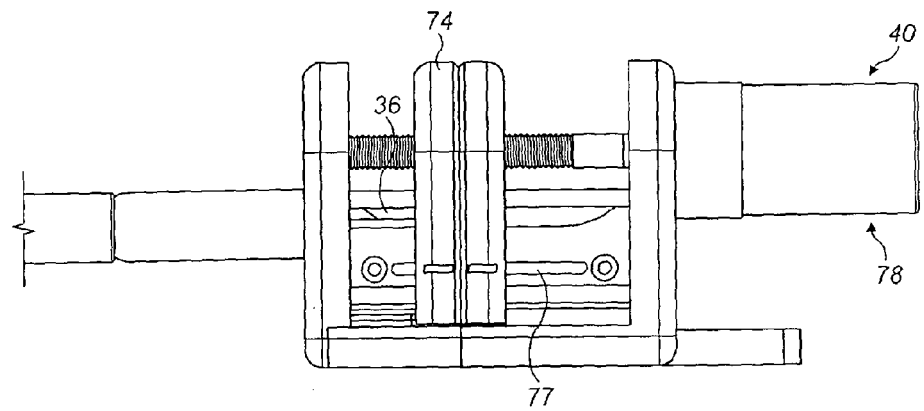
Figure 9:
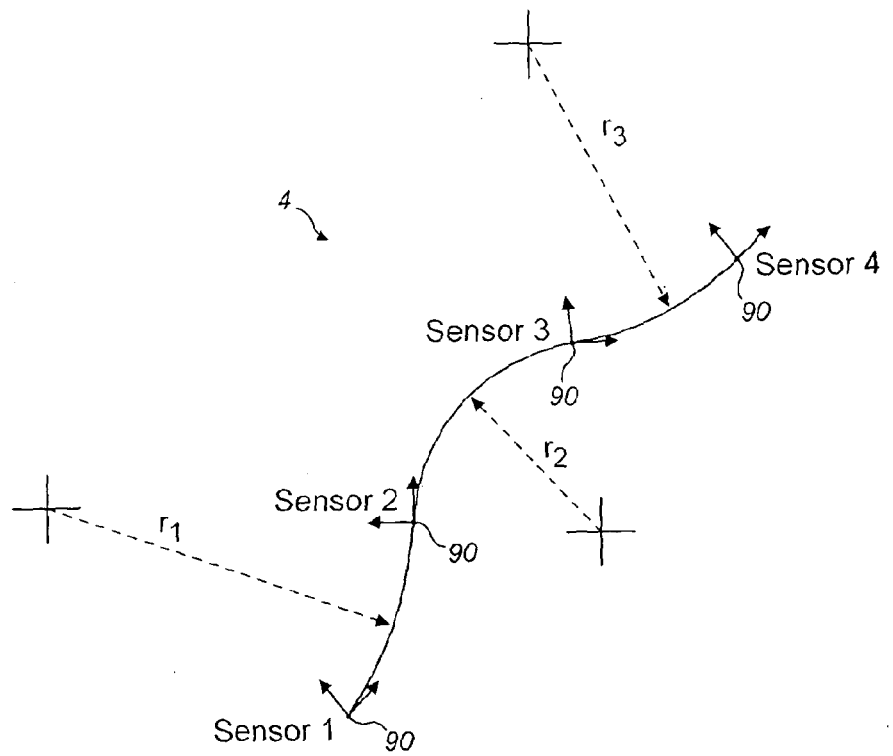
Figure 10:
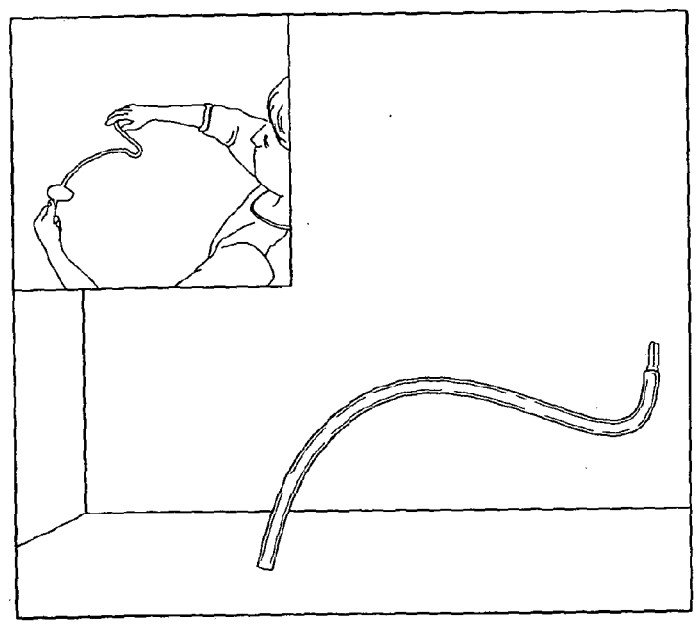
Figure 11:
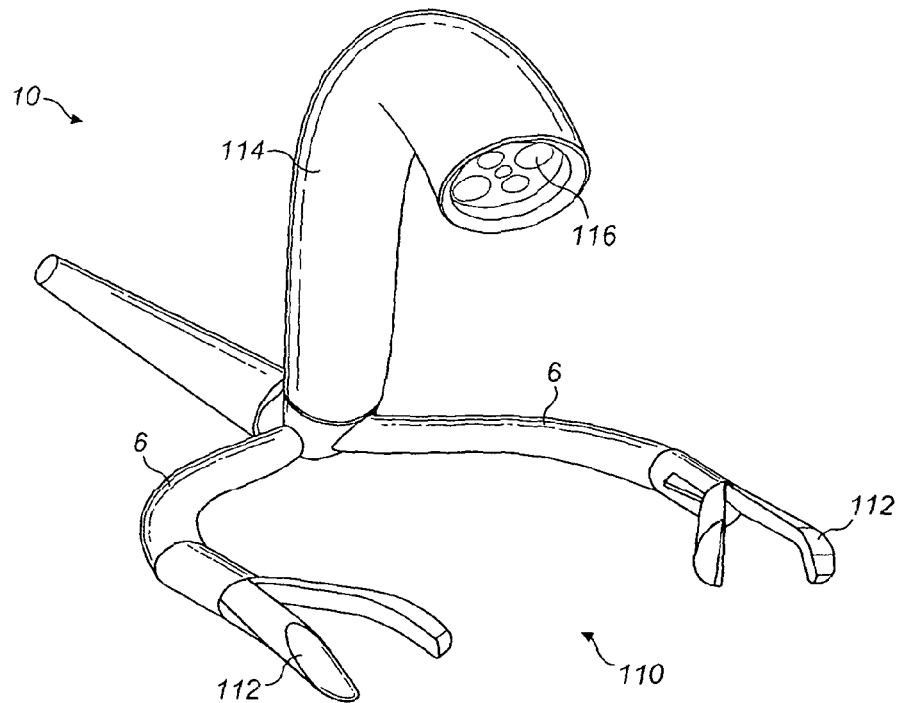
Figure 12:
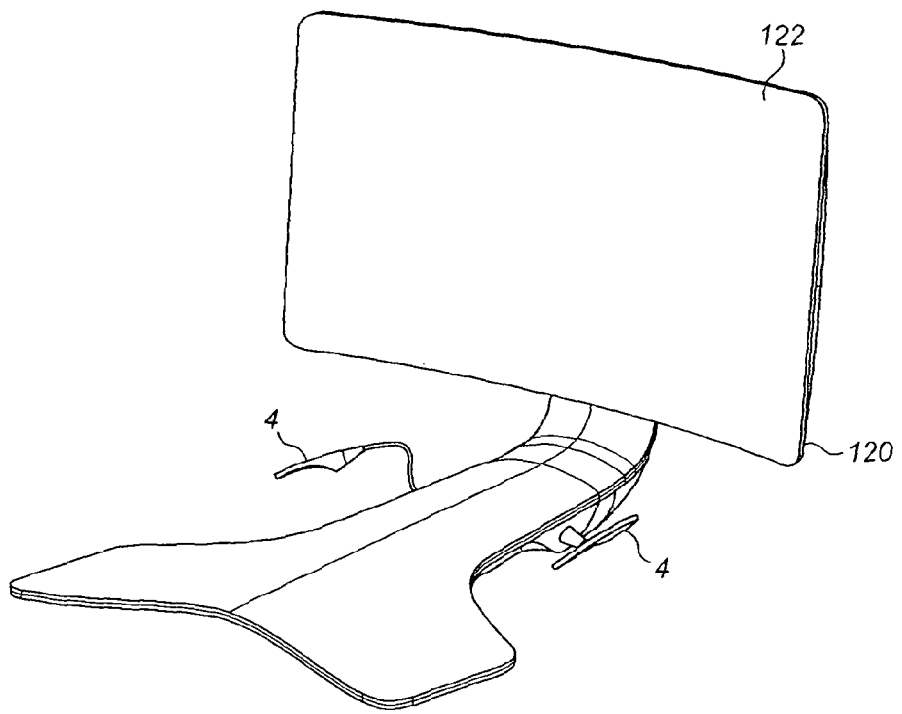
Figure 13A:
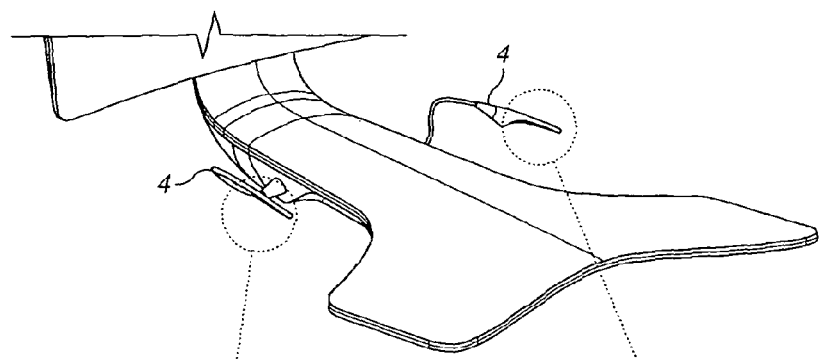
Figure 13B:
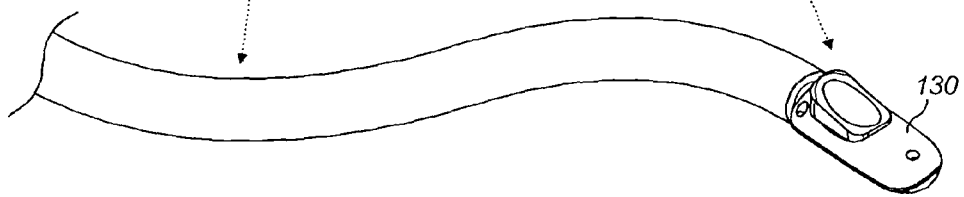
Figure 13C:
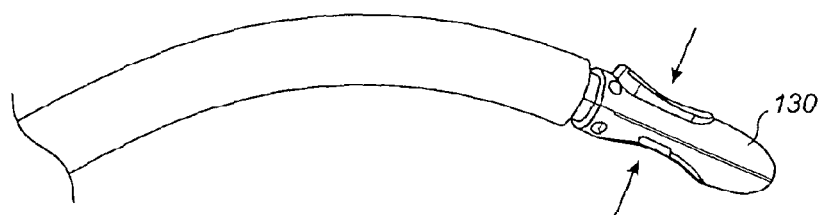
Figure 14A:
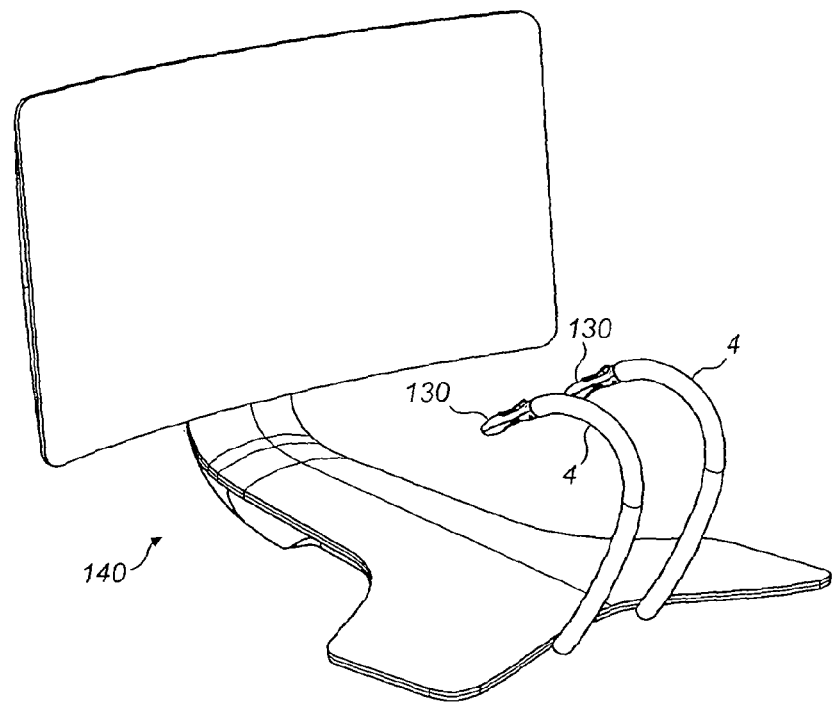
Figure 14B:
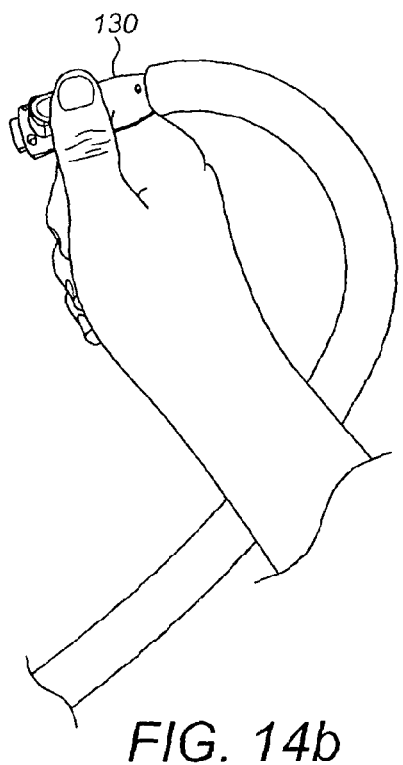

FIGS. 3a, 3b, and 3c each show portions of the master device shown in FIG. 2 which master device comprises a plurality of serially aligned segments with a tendon extending along the length of the device;

FIGS. 4a, 4b, and 4c are schematic representations showing how the elements of the master device may be locked, and unlocked by means of the tendon;

FIG. 5 shows use of the apparatus with active constraint concept;

FIGS. 6a and 6b show partial shape locking of the master device to allow distal manipulation only of both the master and the slave;

FIGS. 7 and 8 are schematic representations showing a linear stage and lead screw used to generated tension in a tendon forming part of the master device of an embodiment in the invention;

FIG. 9 is a schematic representation showing the geometric constraints for reconstructing the tube configuration;

FIG. 10 is a representation of a screen shot of the shape sensing reconstruction produced by means of the present invention;

FIG. 11 is a schematic representation of a particular embodiment of a slave device suitable for use in the apparatus according to the invention;

FIG. 12 is a schematic representation of a master device according to an embodiment of the invention and associated console suitable for controlling the slave device shown in FIG. 11;

FIGS. 13a 13b, and 13c shown how the master device may be incorporated into a console; and FIGS. 14a and 14b show another embodiment of the invention with a particular orientation of the master device.

Figure 1:
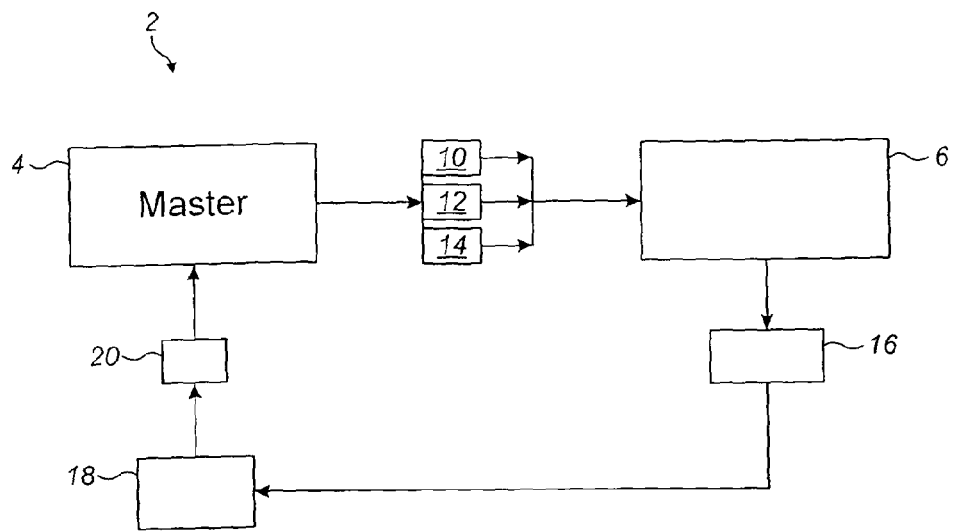
FIG. 1 is a schematic representation of an apparatus according to the present invention.

Referring to FIG. 1 an apparatus according to an embodiment of the invention is designated generally by reference numeral 2. The apparatus comprises a master device 4 which controls a slave device 6. In embodiments of the invention, the shape of both the master device 4 and the slave device 6 is such that movement in the master device 4 maps directly onto the slave device 6 to provide an intuitive system.

The slave device 6 may be in the form of a robotic surgical tool and may for example comprise a hyper-redundant snake like device.

The master device may have a similar shape and may thus have a similar number of degrees of freedom to that of the slave device 6. In other embodiments however, the slave device 6 may have more degrees of freedom than that of the master device 4.

The apparatus further comprises one or more sensors 8 adapted to sense the configuration and/or orientation of the master device throughout operation of the apparatus. In this embodiment of the invention, there are three sensors 10, 12, and 14. The sensors 10 are adapted to measure the acceleration of the master device 4, the sensors 12 are adapted to measure the magnetic field around the master device, and the sensors 14 are adapted to measure the angular rate of movement of the master device.

The sensors 10, 12 and 14 are operatively connected to the slave device 6 such that the slave device is caused to assume a corresponding shape and orientation as the master device throughout operation of the apparatus 2.

The apparatus further comprises a detector 16 for detecting predetermined parameters of, or relating to the slave device. Such parameters could be, for example, the location of the slave device 6, the proximity of any objects to the slave device, and whether or not contact has been made between the slave device and any object (real or virtual). The detector is operatively coupled to an actuator 18 which in turn is operatively connected to a shape locking system 20. If predetermined parameters have been detected by detector 16, the activator is caused to activate the shape locking system 20 and lock the master unit 4 so that it cannot change its shape or configuration until the shape locking system has been released.

The locking of the master device 4 is this way provides a passive haptic interface to the user and prevents further movement of the slave device 6 until the shape locking system has been released.

These components will now be further described with reference to the other Figures.

Referring to FIG. 2, portions of the master device 4 and slave device 6 are shown. FIG. 2 shows that manipulation of the master device 4 by the hands of the operator results in the slave device 6 assuming the same configuration.

In the schematic representation shown FIG. 2, the slave device 6 has been inserted through an incision paint 20 into the body of a patient and is approaching a surgical site 22.

Turning now to FIGS. 3a to 3c and 4a to 4c, the shape locking system according to the invention is explained in more detail.

In embodiments of the invention, the master device 4 comprises a plurality of serially aligned segments 30. Each of these segments comprises a male spherical surface 32 at one end and a female spherical surface 34 at an opposite end. The segments are orientated so that a male spherical surface 32 of a first element will be adjacent to or in contact with a female spherical surface 34 of an adjacent segment. The master device further comprises a tendon 36 extending along the length of the master device 4. In this embodiment of the invention, the tendon 36 runs through a central channel 38 formed in each of the segments 30. The tendon is used to impart compressive loading between the segments which compressive loading will cause the adjacent segments to be pushed together.

This can be seen more clearly in FIGS. 4a to 4c. FIG. 4a shows the master device in a locked position in which the compressive tension has been applied the master device 4 by means of the tendon, and adjacent segments 30 abut one another.

In FIG. 4b, the compressive tension has been removed by unwinding the tendon thus enabling adjacent segments 30 to move away from one another.

When the master device is in the locked position as also shown in FIG. 4c, frictional force is created between adjacent segments and arising from the compressive loading meaning that the master device will resist a lateral load generated by the user.

In order to lock the master device 4, a single actuator 40 only is required. This actuator will be described in more detail herein below. In active haptic devices, an actuator is required per degree of freedom so as to be capable of generating arbitrary forces and/or torques.

This means that devices according to embodiments of the present invention may be made more compact than devices utilising an active haptic interface. A compact device can be advantageous for reducing the system's foot print in the operating theatre.

Further, the continuous nature of the tubular master device 4 and slave device 6 also makes cleaning and sterilisation considerably easier than is the case for other haptic devices with mechanical linkages and visible moving parts. Furthermore, since the device requires only one actuator and may make use of inertial sensors, the device can be made inexpensively and can feasibly be made disposal.

FIG. 5 shows the device being used in conjunction with the "active constraint" concept. In embodiments of the invention used in this way, the apparatus will comprise one or more sensors attached to or positioned close to the slave device 6, or positioned remotely thereto. These sensors will determine when the slave reaches a predetermined boundary and will signal to the actuator of the shape locking system when the slave device reaches such a boundary. Under these conditions, the shape locking system will be activated to lock the master device thereby preventing further movement of both the master device and the slave device.

Turning now to FIGS. 6a and 6b partial locking of the master device 4 is shown, which results in similar partial locking of the slave device 6.

This can be useful in order to allow distal manipulation only of both the master device and the slave device. In other words, the number of degrees of freedom of movement available to the slave device may be reduced in this way in order to ensure more accurate movement of the slave device.

The actuator for the shape locking system in shown in more detail in FIG. 7.

The actuator 40 comprises a lead screw 42 with a linear stage 74 and is driven by motor 78. In order apply tension to the tendon 36, the tendon is fixed to a translatable linear stage and also to the distal segment of the elements 36 of the master device 4.

Tension is transmitted through the tendon which allows the segments to lock together as explained herein above.

In the illustrated embodiment, the tendon is located in the centre of three yokes 76 which constrain the linear stage to have only one linear degree of freedom and to minimise the moment that results from the lead screw and tendon misalignment.

A lead screw is adopted in the illustrated embodiment due to the large load that is required to generate high frictional forces required to make the structure sufficiently stiff to with stand lateral load applied by a user.

In addition, the lead screw is not back driveable which means that the motor 78 does not have to be stalled to maintain a tension in the tendon.

If a friction shape lock approach is adopted, as in the illustrated embodiments, the actuator has to generate a considerable reaction load in the segments which must be many times greater than the "bending" mode subjected to the shape lock mechanism.

This is because, firstly, the friction generated between the segments is proportional to the reaction force and highly dependent on the co-efficient of friction between the elements. Even a high co-efficient of friction (i.e 0.5) means that the reaction force must be twice that of the maximum friction force that can be generated before the segment slips.

Secondly, a long, high aspect ratio "tube" containing many segments will mean that there is large turning moment about the base of the structure, and this to leads to a requirement for a large force to be generated from the actuator.

Given the large axial loads required, it is also desirable to ensure that the lead screw is axially de-coupled from the motor so that the loads are transmitted through a thrust bearing rather than through the motor/gearbox which would cause damage.

In the illustrated embodiment, the actuator 40 comprises a conventional DC motor 78. In other embodiments however other actuators could be used as appropriate.

A position sensor 77 detects a position of the linear stage. The position sensor is used as a soft limit for the lead screw.

The master device may comprise a plurality of shape lockable elements positioned axially along the length of the master device and shaped to engage with one another.

The slave may further comprise a tendon extending along the length of the master device, and through the elements. The device may comprise a plurality of tendons.

The shape locking system may comprise an actuator for introducing tension into the tendon resulting in the segments locking together.

Adjacent segments may be shaped such that a friction shape lock is achieved through the tensioning of the tendon.

Once appropriate tension has been applied to the tendon, adjacent elements will be locked to one another, and the master device will be able to withstand lateral forces applied to it.

In some embodiments of the invention, adjacent elements may comprise corresponding pits and bumps positioned such that when adjacent elements are pulled together through tension within the tendon, a pit formed on a first element will encase with a corresponding bump on an adjacent element, and vice versa.

Such an arrangement will provide a mechanical constraint between adjacent segments when tension is applied to the tendon rather than relying merely on friction between adjacent elements.

In such an embodiment, the master device would have a finite number of configurations in which it would be locked, whereas in an embodiment in which friction locking is relied on without the present of pits and bumps, there are an infinite number of configurations in which the master device could be locked.

Further, in embodiments of the invention comprising interlocking pits and bumps, it will not be possible to gradually apply the shape lock. This means that the master device would either have to be in a purely locked or purely loose state.

Such embodiments of the invention do however benefit from a greatly reduced tensile load that needs to be generated by the actuator used to tension the tendon.

The actuator may comprise any convenient device such as a conventional DC motor, a linear servomotor, pneumatic/hydraulic actuations, solenoid actuation, shape memory alloy, piezoelectric motor, electromagnetic motor etc.

In embodiments of the invention in which the actuator comprises a pneumatic/hydraulic or ultrasonic actuator, the master device could be made to be compatible with MRI systems in order that it could be used when a patient is undergoing an MRI scan, for example.

The apparatus may comprise a plurality of actuators as necessary to apply appropriate tension to the tendon.

In embodiments of the invention in which a single tendon only is used, the tendon may extend substantially along the axis of the master device. In such an embodiment, the tendon will extend substantially through a middle portion of the segments forming the master device. In such an embodiment, there will be minimal change in tendon path length regardless of what configuration the master device is in. However a disadvantage of such an embodiment is that there will be relatively small bend radius defined by the segments forming the master device before the tendon will catch on a portion of the segments. This will have the effect of the tendon trying to straighten out the shape lock segments.

In embodiments of the invention where a plurality of tendons are present, each tendon would be spaced apart from the axis of the master device and thus be positioned in a peripheral portion of each of the segments forming the master device. In such an embodiment, the tendons may be selectively tensioned in order to reduce the minimum bend radius.

In such embodiments of the invention, a plurality of actuators would be required, and the tendons would have to adopt a compensation method.

One way of sensing the shape of the master device will now be described.

In the embodiments illustrated, the shape of the master device 4 may be considered as a tube. The configuration of the tube is approximated from inertial measurements using inertial measurement units (IMUs). In the illustrated embodiments, multiple sensors 90 are placed along the length of the tube as shown in FIG. 9. These sensors can measure three orientations relative to a global co-ordinate system.

Accelerometers can be used measure the orientation of the master device at different positions along the device, relative to the field of gravity. Magnetic field sensors are adapted to measure the sensor orientation in the plane normal to gravity.

Set out below is a shaped sensing analysis.

To facilitate our analysis, three coordinate systems are defined (capital X, Y, Z are used to represent the coordinate system):
1. Global coordinate frame G: the reference coordinate system,
2. Tube (the haptic device) coordinate frame B: it is attached at some arbitrary point along the tube.
3. Sensor coordinate frame S: it corresponds to the axes of three orthogonally mounted inertial sensors and a magnetometer in the sensor unit, and all the sensor measurements are expressed in this coordinate system.

To simplify our analysis, we define $R_s^b$ as the rotation between the local 'tube' coordinate system and the corresponding sensor coordinate system.

Process Model

Since the basic purpose of this analysis is to estimate the rotational movement of a 'tube', orientation should be explicitly included in the state vector. In this analysis, we choose Euler angles to represent orientation of each point of the 'tube' where a sensor is present, where $\phi$, $\theta$ and $\psi$, called roll, pitch, yaw respectively, represent positive rotations about the X, Y, and Z 'tube' axes respectively. The transformation from the global frame to the 'tube' frame can be defined by three successive rotations as:

$$R(\phi,\theta,\psi) = R_Z(\psi) R_Y(\theta) R_X(\phi) \tag{1}$$

where $$R_X(\phi) = \begin{bmatrix} 1 & 0 & 0 \\ 0 & \cos(\phi) & -\sin(\phi) \\ 0 & \sin(\phi) & \cos(\phi) \end{bmatrix} \tag{2}$$

$$R_Y(\theta) = \begin{bmatrix} \cos(\theta) & 0 & \sin(\theta) \\ 0 & 1 & 0 \\ -\sin(\theta) & 0 & \cos(\theta) \end{bmatrix} \tag{3}$$

and $$R_Z(\psi) = \begin{bmatrix} \cos(\psi) & -\sin(\psi) & 0 \\ \sin(\psi) & \cos(\psi) & 0 \\ 0 & 0 & 1 \end{bmatrix} \tag{4}$$

Given the angular rate $\omega(t)$, the Euler angle integration kinematics can be written as:

$$\dot{\Theta}(t) = W(\Theta(t))\omega(t) \tag{5}$$

where $W(\Theta(t))$ is the Jacobian matrix that relates the absolute rotation angle to the angular rate, $$\Theta(t) = \begin{bmatrix} \phi(t) \\ \theta(t) \\ \psi(t) \end{bmatrix}$$

$$\omega(t) = \begin{bmatrix} \omega_X(t) \\ \omega_Y(t) \\ \omega_Z(t) \end{bmatrix}$$

The relationship between Euler angles and angular rate can be expressed as:

$$\begin{bmatrix} \omega_X(t) \\ \omega_Y(t) \\ \omega_Z(t) \end{bmatrix} = \begin{bmatrix} \dot\phi(t) \\ 0 \\ 0 \end{bmatrix} + R_X(\phi(t)) \begin{bmatrix} 0 \\ \dot\theta(t) \\ 0 \end{bmatrix} + R_X(\phi(t)) R_Y(\theta(t)) \begin{bmatrix} 0 \\ 0 \\ \dot\psi(t) \end{bmatrix} \quad (6)$$

and then we can get:

$$W(\Theta(t)) = \begin{bmatrix} 1 & \sin(\phi(t))\tan(\theta(t)) & \cos(\phi(t))\tan(\theta(t)) \\ 0 & \cos(\phi(t)) & -\sin(\phi(t)) \\ 0 & \sin(\phi(t))/\cos(\theta(t)) & \cos(\phi(t))/\cos(\theta(t)) \end{bmatrix} \quad (7)$$

For each point along the 'tube' where a sensor is present, we define the following 6×1 vector as the state:

$$x_t = \begin{bmatrix} \Theta(t) \\ \omega(t) \end{bmatrix} \quad (8)$$

With the state, the process model can be expressed as a linear combination of:

$$x_{t+1} = Fx_t + Ge_t \quad (9)$$

where $$F = \begin{bmatrix} I_{3\times 3} & W(\Theta(t))\Delta t \\ 0 & I_{3\times 3} \end{bmatrix} \quad (10)$$

and $$G = \begin{bmatrix} W(\Theta(t))\Delta t^2/2 \\ \Delta f \end{bmatrix} \quad (11)$$

$\Delta t$ is the sampling period, $I_{3\times 3}$ is the identity matrix of order 3, and $e_t$ is the angular acceleration, which is assumed to be zero mean Gaussian noise with variance Q.

Measurement Model

The measurement model relates the measurement value z to the value of the state vector x. The sensor unit provides three types of measurement: acceleration, magnetic field and angular rate. The generalized form of the measurement equation h is $$z_t = \begin{pmatrix} z_t^a \\ z_t^m \\ z_t^g \end{pmatrix} = h(x_t) + v_t = h(x_t) + \begin{pmatrix} v_t^a \\ v_t^m \\ v_t^g \end{pmatrix} \quad (12)$$

where $v_t$ is assumed to be zero mean additional gaussian white noise with covariance matrix V, $z_t^a$, $z_t^m$ and $z_t^g$ are all the acceleration, magnetic field and angular rate measurements respectively.

As the movement of 'tube' is relatively stable, the 3-axis accelerometer predominantly measure the gravity field vector with respect to global coordinate system resolved in sensor local coordinate system. Define $g=[g_x, g_y, g_z]^T$ as the vector of the gravitational field resolved in global coordinate system, and then the expected measurements of these fields are given by the transformation of g to the local sensor coordinate system, which can be represented as:

$$z_t^a = \begin{pmatrix} z_t^{a,X} \\ z_t^{a,Y} \\ z_t^{a,Z} \end{pmatrix} = R_s^b R(\phi(t), \theta(t), \psi(t))g + v_t^a \quad (13)$$

where $v_t^a$ the acceleration measurement noise.

With the proposed sensor configuration, the magnetometer measures the magnetic field. The expected measurements of this field are given by the transformation of the global magnetic field to the local sensor coordinate system. Similar to accelerometer's measurement, define $m=[m_x, m_y, m_z]^T$ as the vector of the magnetic field resolved in global coordinate system, and then the sensor measurement can be written as:

$$z_t^m = \begin{pmatrix} z_t^{m,X} \\ z_t^{m,Y} \\ z_t^{m,Z} \end{pmatrix} = R_s^b R(\phi(t), \theta(t), \psi(t))m + v_t^m \quad (14)$$

where $v_t^m$ is the acceleration measurement noise.

Gyroscopes measure angular velocity in the local frame of each sensor. The angular velocity $\omega_t$ is already part of the state vector, leading to a simple model that relates the measured angular rate to the state as:

$$z_t^g = \begin{pmatrix} z_t^{g,X} \\ z_t^{g,Y} \\ z_t^{r,Z} \end{pmatrix} = R_s^b H x_t + v_t^g \quad (15)$$

where $H=[0\ I_{3\times 3}]$ and $v_t^g$ the angular rate measurement noise.

Kalman Filtering

In general, the Kalman filter operates on a probability distribution in the state vector space, which is characterized by its first and second order statistical moments: mean and covariance. The process and measurement models predict and update this distribution. Unfortunately, the Kalman filter can only deal with linear and Gaussian problems, while the measurement equations here are nonlinear. The solution to this problem is the usage of an extension to the classical Kalman filter, namely the unscented Kalman filter (UKF) which can deal with non-linearity well.

At time t−1, we will get the Maximum A Posterior (MAP) estimation of the state vector x by a Gaussian distribution $N(\mu_{t-1}, \Sigma_{t-1})$. We can construct another Gaussian distribution for UKF recursion, and the mean is $x_{t-1}^a = [\mu_{t-1}^T, 0, 0]^T$, while the covariance matrix is $$P_{t-1}^a = \begin{bmatrix} \Sigma_{t-1} & 0 & 0 \\ 0 & Q & 0 \\ 0 & 0 & V \end{bmatrix}$$

The constructed Gaussian distribution can be represented by a set of 2L+1 sample points $X_{t-1}^i$ and weights $W_{t-1}^i$, denoted as sigma points $(X_{t-1}^i, W_{t-1}^i)$, where I=1, 2, L, 2L+1, $L=n_x+n_v$ and $n_e$ and $n_v$ are the dimensional of state vector x, state noise e and measurement noise v respectively. Let $\lambda=\alpha^2(L+\kappa)-L$ and do the scaled unscented transformation, the sigma points will be $$X_{t-1}^0 = x_{t-1}^a \quad (16)$$

$$X_{t-1}^i = x_{t-1}^a + \left(\sqrt{(L+\lambda)P_{t-1}^a}\right)_i,$$

$$i = 1, 2, \ldots, L$$

$$X_{t-1}^i = x_{t-1}^a - \left(\sqrt{(L+\lambda)P_{t-1}^a}\right)_{i-L},$$

$$i = L+1, \ldots, 2L$$

$$W_{t-1}^{0,m} = \lambda/(L+\lambda)$$

$$W_{t-1}^{0,c} = \lambda/(L+\lambda) + (1-\alpha^2+\beta)$$

$$W_{t-1}^{i,m} = W_{t-1}^{i,c} = \frac{1}{2(L+\lambda)},$$

$$j = 1, \ldots, 2L$$

where $\kappa$, $\alpha$, $\beta$ are positive scaling parameters and $(\sqrt{(L+\lambda)P_{t-1}^a})$, is the ith row or column of the matrix square root of $(L+\lambda)P_{t-1}^a$ and $W_{t-1}^i$ is the weight associated with the ith point. Then the mean $\mu_t$ and covariance $\Sigma_t$ of the state vector $X_t$ propagate as follows: First the prediction step is performed as $$X_{i,t|t-1}^X = FX_{i,t-1}^X + GX_{i,t-1}^W \quad (17)$$

$$\mu_{t|t-1} = \sum_{i=0}^{2L} W_{t-1}^{i,m} X_{i,t|t-1}^X$$

$$\tilde{\mu}_{i,t|t-1} = X_{i,t|t-1}^X - \mu_{t|t-1}$$

$$\sum_{t|t-1} = \sum_{j=0}^{2L} W_{t-1}^{i,c} (\tilde{\mu}_{t|t-1}^i)(\tilde{\mu}_{t|t-1}^i)^T$$

$$\gamma_{i,t|t-1} = h(X_{i,t|t-1}^X) + X_{i,t-1}^V$$

$$\bar{z}_{t|t-1} = \sum_{i=0}^{2L} W_{t-1}^{i,m} \gamma_{i,t|t-1}$$

where $X_{t-1}^i = [(X_{i,t|t-1}^x)^T, (X_{i,t|t-1}^W)^T, (X_{i,t|t-1}^V)^T]^T$, then update step is as follows:

$$\mu_t = \mu_{t|t-1} + \text{Gain}_t \cdot (z_t - \bar{z}_{t|t-1})$$

$$\Sigma_t = \Sigma_{t|t-1} - \text{Gain}_t \cdot K_t \cdot (\text{Gain}_t)^T \quad (18)$$

where:

$$\tilde{z}_{i,t|t-1} = \gamma_{i,t|t-1} - \bar{z}_{t|t-1} \quad (19)$$

$$K_t = \sum_{i=0}^{2L} W_{t-1}^{i,c} (\tilde{z}_{i,t|t-1})(\tilde{z}_{i,t|t-1})^T$$

$$\text{Cov}_{t|t-1} = \sum_{i=0}^{2L} W_{t-1}^{i,c} \tilde{\mu}_{i,t|t-1} \tilde{z}_{i,t|t-1}$$

$$\text{Gain}_t = \text{Cov}_{t|t-1} \cdot (K_t)^{-1}$$

and in the process of numerical calculation, some symbols are defined as:

$$\mu_{t|t-1} \triangleq \mathbb{E}(x_t|\bar{z}_{1:t-1}), \mu_t \triangleq \mathbb{E}(x_t|\bar{z}_{1:t}), \bar{z}_{t|t-1} \triangleq \mathbb{E}(\bar{z}_t|\bar{z}_{1:t-1}), \Sigma_{t|t-1} \triangleq \text{cov}(x_t|\bar{z}_{1:t-1}), \Sigma_t \triangleq \text{cov}(x_t|\bar{z}_{1:t}) \text{ and } K_t \triangleq \text{cov}(\bar{z}_t|\bar{z}_{1:t-1}).$$

It is assumed that the tube is continuous so the curves that join the tube together are tangential to each other at a sensor location.

It is also assume that the curved region between the sensors is of a constant radius.

Since the distance between the sensors 90 is known (i.e. the arc length), the tube profile can be reconstructed in three dimensions as shown in FIG. 10.

Whilst it is assumed that in this embodiment the radius of curve between sensors is constant, the algorithm used to sense the shape of the master device can be modified so as to include consideration for mechanical behaviour by for example applying the beam theory.

Further embodiments of an apparatus according to the present invention are illustrated in FIGS. 11, 12, 13*a-c* and 14*a-b*.

Referring first to FIG. 11, an apparatus according to the invention is designated generally by the reference numeral 110. Only a portion of the apparatus 110 is shown in FIG. 11, and the master unit is not visible. FIG. 11 illustrates two slave devices 6 each in the form of a snake-like tube device having an instrument 112 extending from each slave device 6, which instruments are manipulatable via the master unit. The device further comprises a flexible portion 114 comprising a plurality of modules which may be driven by means of tendons for example. The flexible portion 114 carries LEDs 116 as well as cameras (not shown).

Such an arrangement is described in more detail in our co-pending patent application nos. GB 1107939.9 and GB 1112228.0.

Referring now to FIG. 12, an embodiment of a master device is shown. The master unit comprises two master devices 4 of the type described hereinabove positioned such that a surgeon may comfortably hold an individual device in each hand. Movement of each of the devices 4 will result in corresponding movement of a slave device of the type shown in FIG. 11, for example.

A surgeon is able to view movement of the slave devices on a screen 120 forming part of the master console 122.

FIGS. 13*a, b* and *c* show further embodiments of the invention. In the embodiment illustrated in these figures, a master console unit comprises two master devices 4 of the type described hereinabove. Each of these devices comprises a pinch grip at a proximal end thereof designated generally by the reference numeral 130. A surgeon is able to pinch, or grip these grippers 130 in order to manipulate a slave device.

A further embodiment of the invention as shown in FIGS. 14*a* and 14*b* in which a master console unit is designated generally by the reference numeral 140. The master unit 140 comprises two master devices 4 of a type described hereinabove each of which has a gripper of the type illustrated in FIGS. 13b and 13c. The configuration of each of the master devices 4 provides a particularly ergonomic instrument for use by a surgeon.

The apparatus of the present invention therefore provides an intuitive surgical device for minimal invasive surgery procedures.

The invention claimed is:

1. Apparatus for Minimal Invasive Surgery (MIS) comprising
   a master device,
   a slave device,
   a detector for detecting a parameter of, or associated with, the slave device, and
   a shape locking system for locking the shape of the master device in response to a parameter detected by the detector, wherein the apparatus further comprises a detector adapted to detect when the slave device touches or moves close to a boundary and for signaling to the shape locking system when the slave device has come within a predetermined distance or is touching the boundary.

2. An apparatus according to claim 1 wherein the master device and the slave device are operatively connected to one another such that movement of the master device maps directly onto the slave device.

3. Apparatus according to claim 2 wherein the master device and the slave device each have the same architecture.

4. Apparatus according to claim 3 wherein the master device and the slave device each comprise a hyper redundant robot.

5. An apparatus according to claim 1 wherein the detector comprises a sensor adapted to measure contact forces and/or torques applied to the slave device.

6. An apparatus according to claim 1 wherein the shape locking system is adapted to lock a portion only of the master device.

7. An apparatus according to claim 1 comprising a trigger to enable an operator of the apparatus to activate the shape locking system either partially or totally.

8. Apparatus according to claim 7 further comprising an actuator for actuating the shape locking system.

9. An apparatus according to claim 8 wherein the master device comprises a plurality of shape-lockable elements positioned axially along the length of the master device, which elements are shaped to engage with one another.

10. An apparatus according to claim 9 comprising a tendon extending along the length of the master device.

11. An apparatus according to claim 10 wherein the actuator is operatively connected to the tendon and is adapted to introduce tension into the tendon in order to activate the shape locking system.

12. An apparatus according to claim 9 wherein each shape lockable element comprises a lock portion adapted to engage with the corresponding lock portion on an adjacent element.

13. An apparatus according to claim 12 wherein each element comprises a plurality of lock portions each of which lock portions is adapted to engage with the corresponding one of a plurality lock portions on adjacent element.

14. An apparatus according to claim 13 wherein each element comprises a plurality of pits at one end thereof, and bump an opposite end thereof, the pits being shaped to locate and engage with corresponding bumps on an adjacent element, and vice versa.

15. An apparatus according to claim 13 further comprising a sensor for sensing the shape of the master device.

16. An apparatus according to claim 15 wherein the sensor comprises one or more of: an inertial sensor; an accelerometer; a gyroscope; and magnetometer.

17. Apparatus according to claim 16 wherein the actuator includes a motor.

18. Apparatus according to claim 17 further comprising a master console operatively positioned between the master device and the slave device.

19. A method for carrying out minimal invasive surgery using an apparatus, comprising
   providing a master device and a slave device,
   causing a detector to detect a parameter of, or associated with, the slave device,
   causing a shape locking system to lock the shape of the master device in response to a parameter detected by the detector; and
   causing a detector to detect when the slave device touches or move close to a boundary and causing the detector device to signal to the shape locking system when the slave device has come within a predetermined distance or is touching the boundary.

\* \* \* \* \*